United States Patent
Hasegawa et al.

[11] Patent Number: 5,854,183
[45] Date of Patent: Dec. 29, 1998

[54] GREASE COMPOSITION FOR CONSTANT-VELOCITY JOINTS

[75] Inventors: Yukio Hasegawa; Shinichi Takabe, both of Iwata; Hirotsugu Kinoshita, Yokohama; Souichi Nomura, Yokohama; Fumihiro Itano, Yokohama, all of Japan

[73] Assignees: Nippon Oil Co., Ltd., Tokyo; NTN Corporation, Osaka, both of Japan

[21] Appl. No.: 844,952

[22] Filed: Apr. 23, 1997

[30] Foreign Application Priority Data

Apr. 26, 1996 [JP] Japan ................................ 8-131426

[51] Int. Cl.$^6$ .................. C10M 115/08; C10M 141/10; C10M 141/12; C10M 141/06
[52] U.S. Cl. ................. 508/316; 508/364; 508/434; 508/442; 508/464; 508/552
[58] Field of Search .................... 508/316, 364, 508/434, 442, 464, 552

[56] References Cited

U.S. PATENT DOCUMENTS

| | | | |
|---|---|---|---|
| 4,501,678 | 2/1985 | Katayama et al. | 508/364 |
| 4,840,740 | 6/1989 | Sato et al. | 508/364 |
| 4,915,860 | 4/1990 | Kinoshita et al. | 508/364 |
| 5,043,085 | 8/1991 | Kinoshita et al. | 508/316 |
| 5,589,444 | 12/1996 | Hatakeyama | 508/552 |
| 5,604,187 | 2/1997 | Takeuchi et al. | 508/552 |
| 5,607,906 | 3/1997 | Okaniwa et al. | 508/552 |
| 5,612,297 | 3/1997 | Kamakura et al. | 508/364 |
| 5,631,213 | 5/1997 | Tanaka et al. | 508/364 |

*Primary Examiner*—Jerry D. Johnson
*Attorney, Agent, or Firm*—Kubovcik & Kubovcik

[57] ABSTRACT

A grease composition for constant-velocity joints which is prepared by blending a lube base oil with (A) a urea-urethane thickening agent comprising a mixture of (a) 20 to 95 mole % of a diurea compound of the formula (1):

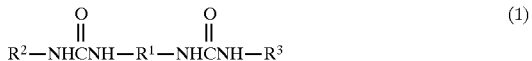

(b) 4 to 50 mole % of a urea-urethane compound of the formula (2):

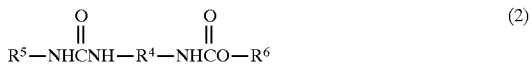

and (c) 1 to 50 mole % of a diurethane compound of the formula (3):

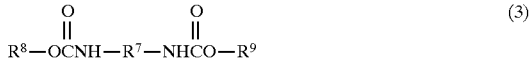

with each mole percentage being based on the total amount of the components (a) to (c), wherein a ratio of the total number of $R^2$—NH—, $R^3$—NH— and $R^5$—NH— groups contained in the mixture to the total number of $R^6$—O—, $R^8$—O— and $R^9$—O— groups contained therein lies between 40:60 and 95:5, (B) at least one compound selected from oxidized paraffins, diphenyl hydrogenphosphite and hexamethylphosphoric triamide, and (C) at least one organomolybdenum compound selected from molybdenum dithiophosphate and molybdenum dithiocarbamate.

10 Claims, 1 Drawing Sheet

GREASE COMPOSITION FOR CONSTANT-VELOCITY JOINTS

BACKGROUND OF THE INVENTION

1. Field of the Invention

This invention relates to a grease composition for constant-velocity joints and more specifically to such a composition particularly suitable for tripod type constant-velocity joints.

2. Prior Art

Tripod type constant-velocity joints include plunging type constant-velocity joints. These tripod type joints are fundamentally composed of a trunnion having three axes on the same plane, three rollers and a tulip having three cylindrical grooves with which the rollers are engaged and they have such characteristics that the driven shaft is eccentric to the driving shaft in an amount corresponding to the joint angle and that the driving shaft revolves over a rotation angle three times the rotation angle of the driven shaft thereby to enable the tripod type joints to maintain their constant-velocity. Such tripod type constant-velocity joints are frequently used particularly for the shafts transmitting a driving force from an automotive transmission to tires. There has been heretofore used a grease composition prepared by adding a thickening agent (such as a lithium soap or urea) and various additives to a lube base oil.

Tripod type constant-velocity joints are proposed with such a property due to their structure that a force (this force being hereinafter referred to as "induced thrust") is generated in the direction of axis of the joints owing to the sliding friction resistance occurring in the inside of the joints, when a rotary torque is transmitted at an operating angle. When the cycle of generation of the induced thrust coincides with the inherent frequency of an engine, car body or suspension in a car, the car body will cause resonance to result in causing shudder and giving an uncomfortable feeling to passengers. Accordingly, it has been sought to lower the induced thrust as much as possible and to keep a low-level induced thrust even after long-time revolution.

Further, there is a recent tendency for the torque applied to the joint to increase with an increasing engine displacement of a car. However, constant-velocity joints lubricated with current greases have raised a problem that an induced thrust will increase with an increase in the torque.

Japanese Patent Appln. Laid-Open Gazette No. 46299/88, on the other hand, has proposed a grease composition for constant-velocity joints prepared by adding an organomolybdenum compound to a grease composition containing a urea compound as the thickening agent, in an attempt to suppress the induced thrust to a low level. Even the grease composition so proposed, however, causes a variation and/or an increase in the induced thrust with the lapse of revolution time, though it can lower the induced thrust in the initial stage. Thus, the proposed grease composition cannot satisfactorily solve the above problem and is desired to be further improved.

The inventors of this invention have intensively studied to find that the above problem can be solved by adding a specific thickening agent and additives having specific structures to a base oil. This invention has been accomplished on the basis of this finding.

This invention aims at providing a grease composition for constant-velocity joints which can suppress the induced thrust to a low level not only when the joints are used under a low torque but also when they are used under a high torque and which can keep the low-level induced thrust even after long-time revolution.

SUMMARY OF THE INVENTION

This invention has its object to provide a grease composition for constant-velocity joints which is prepared by blending a lube base oil with (A) a urea-urethane thickening agent comprising a mixture of (a) 20 to 95 mole % of a diurea compound represented by the following general formula (1):

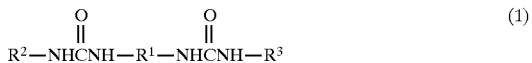

(b) 4 to 50 mole % of a urea-urethane compound represented by the following general formula (2):

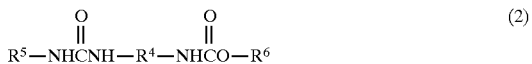

and (c) 1 to 50 mole % of a diurethane compound represented by the following general formula (3):

with each mole percentage being based on the total amount of the components (a) to (c), wherein in the above formulae (1) to (3), $R^1$, $R^4$ and $R^7$ are each independently a divalent aromatic hydrocarbon group having 6 to 15 carbon atoms; and $R^2$, $R^3$, $R^5$, $R^6$, $R^8$ and $R^9$ are each independently cyclohexyl group, a cyclohexyl derivative group having 7 to 12 carbon atoms, or an alkyl or alkenyl group having 8 to 20 carbon atoms, and wherein in said mixture a ratio of the number of amino groups (i.e., the total number of $R^2$—NH—, $R^3$—NH— and $R^5$—NH— groups) to the number of alkoxy groups (i.e., the total number of $R^6$—O—, $R^8$—O— and $R^9$—O— groups) lies between 40:60 and 95:5, (B) at least one compound selected from the group consisting of oxidized paraffins, diphenyl hydrogenphosphite and hexamethylphosphoric triamide, and (C) at least one organomolybdenum compound selected from the group consisting of molybdenum dithiophosphate and molybdenum dithiocarbamate.

DESCRIPTION OF THE PREFERRED EMBODIMENTS

Figure 1:
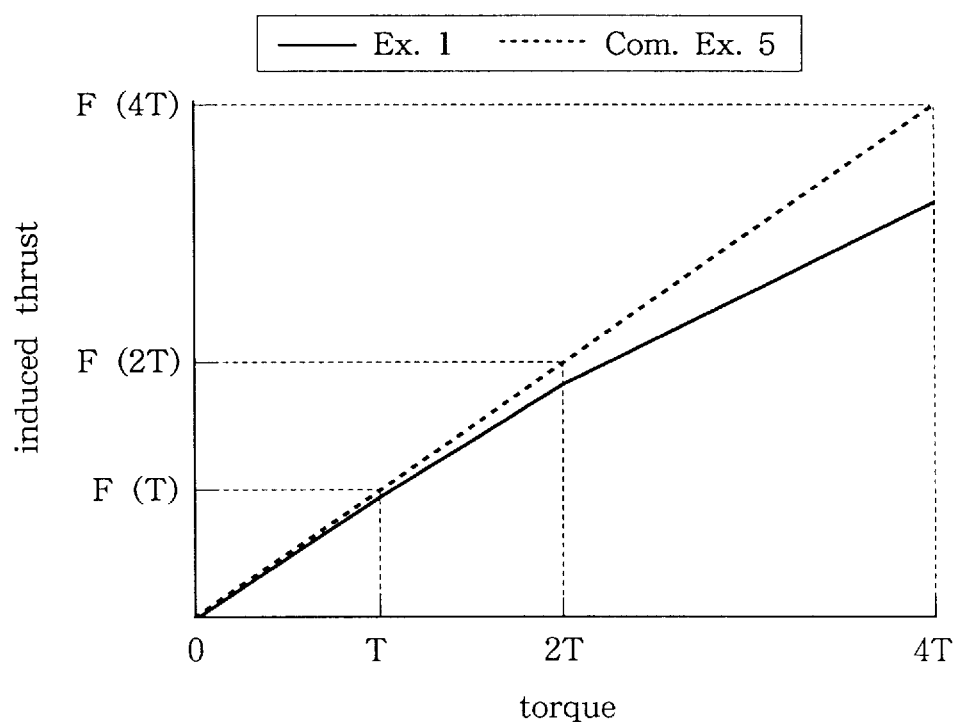
FIG. 1 a graph showing relationship between induced thrust and torque.

The lube base oil contained in the grease composition for constant-velocity joints according to this invention is not particularly limited, but may be any one selected from conventional mineral oils and synthetic base oils as far as they are used as lubricating oils.

Examples of the mineral lube base oils are paraffin base oils and naphthene base oils each produced by refining the lubricating oil fraction obtained by the atmospheric or vacuum distillation of crude oil by a suitable combination of two or more treatments such as solvent deasphalting, solvent extraction, hydrocracking, solvent dewaxing, catalytic dewaxing, hydrofinishing, sulfuric acid washing and clay treatment.

On the other hand, specific examples of the synthetic lube base oils are polyolefins (such as polybutene, 1-octene oligomer, 1-decene oligomer and ethylene-propylene copolymer) and hydrogenated products thereof; alkylbenzenes; alkylnaphthalenes; diesters (such as ditridecyl glutarate, di-2-ethylhexyl adipate, diisodecyl adipate, ditridecyl adipate, and di-2-ethylhexyl sebacate); polyesters (such as trimellitates); polyol esters (such as trimethylolpropane caprylate, trimethylolpropane pelargonate, pentaerythritol-2-ethylhexanoate and pentaerythritol pelargonate); polyoxyalkylene glycols; polyphenyl ethers; and dialkyldiphenyl ethers. These base oils may be used singly or in the form of a mixture of two or more of them.

The lube base oil to be used in this invention may have an arbitrary viscosity. From the standpoint of the ability to keep the induced thrust of constant-velocity joints at a low level even after long-time revolution, however, it is generally desirable that the lower limit of the kinematic viscosity at 100° C. is 5 mm$^2$/s, more desirably 8 mm$^2$/s, most desirably 11 mm$^2$/s, while the upper limit thereof is 30 mm$^2$/s, more desirably 25 mm$^2$/s, most desirably 20 mm$^2$/s.

The component (A), which is the urea-urethane thickening agent contained in the grease composition of this invention, comprises a mixture of (a) a diurea compound represented by the following general formula (1):

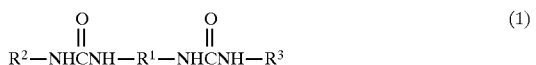

(b) a urea-urethane compound represented by the following general formula (2):

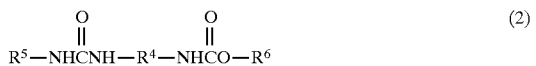

and (c) a diurethane compound represented by the general formula (3):

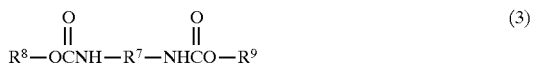

In the above formulae (1) to (3), $R^1$, $R^4$ and $R^7$ are each independently a divalent aromatic hydrocarbon group having 6 to 15 carbon atoms. The term "are each independently" used in this specification refers to "may be identical with or different from".

Particularly preferable examples of the divalent aromatic hydrocarbon group are as follows:

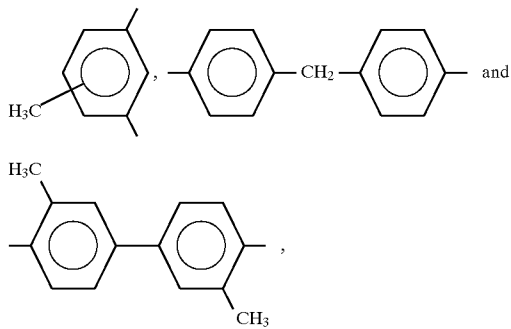

though other divalent aromatic groups having 6 to 15 carbon atoms also enable the grease composition of this invention to exhibit excellent performance.

In the above formulae (1) to (3), $R^2$, $R^3$, $R^5$, $R^6$, $R^8$ and $R^9$ are each independently cyclohexyl group, a cyclohexyl derivative group having 7 to 12 carbon atoms, or an alkyl or alkenyl group having 8 to 20 carbon atoms.

Specific examples of the cyclohexyl group and the cyclohexyl derivative group having 7 to 12 carbon atoms are cyclohexyl group, methylcyclohexyl groups (including all of the substitutional isomers thereof), dimethylcyclohexyl groups (including all of the substitutional isomers thereof), ethylcyclohexyl groups (including all of the substitutional isomers thereof), diethylcyclohexyl groups (including all of the substitutional isomers thereof), linear and branched propylcyclohexyl groups (including all of the substitutional isomers thereof), linear and branched butylcyclohexyl groups (including all of the substitutional isomers thereof), linear and branched pentylcyclohexyl groups (including all of the substitutional isomers thereof), and linear and branched hexylcyclohexyl groups (including all of the substitutional isomers thereof). Among these groups, the cyclohexyl group and the cyclohexyl derivative group having 7 to 8 carbon atoms are particularly preferable from the standpoints of their easy availability and low-cost. Examples of the cyclohexyl derivative group having 7 to 8 carbon atoms are methylcyclohexyl groups (including all of the substitutional isomers thereof), dimethylcyclohexyl groups (including all of the substitutional isomers thereof) and ethylcyclohexyl groups (including all of the substitutional isomers thereof).

Specific examples of the alkyl and alkenyl group having 8 to 20 carbon atoms are linear and branched alkyl groups such as linear and branched octyl groups, linear and branched nonyl groups, linear and branched decyl groups, linear and branched undecyl groups, linear and branched dodecyl groups, linear and branched tridecyl groups, linear and branched tetradecyl groups, linear and branched pentadecyl groups, linear and branched hexadecyl groups, linear and branched heptadecyl groups, linear and branched octadecyl groups, linear and branched nonadecyl groups, and linear and branched icosyl groups; and linear and branched alkenyl groups such as linear and branched octenyl groups, linear and branched nonenyl groups, linear and branched decenyl groups, linear and branched undecenyl groups, linear and branched dodecenyl groups, linear and branched tridecenyl groups, linear and branched tetradecenyl groups, linear and branched pentadecenyl groups, linear and branched hexadecenyl groups, linear and branched heptadecenyl groups, linear and branched octadecenyl groups, linear and branched nonadecenyl groups, and linear and branched icosenyl groups. Among these groups, linear and branched alkyl and alkenyl groups having 12 to 19 carbon atoms are preferable from the standpoints of their easy availability and low-cost. Examples of the alkyl and alkenyl groups having 12 to 19 carbon atoms are linear and branched dodecyl groups, linear and branched tridecyl groups, linear and branched tetradecyl groups, linear and branched pentadecyl groups, linear and branched hexadecyl groups, linear and branched heptadecyl groups, linear and branched octadecyl groups, linear and branched nonadecyl groups, linear and branched dodecenyl groups, linear and branched tridecenyl groups, linear and branched tetradecenyl groups, linear and branched pentadecenyl groups, linear and branched hexadecenyl groups, linear and branched heptadecenyl groups, linear and branched octadecenyl groups, and linear and branched nonadecenyl groups.

In this invention, it is more desirable from the standpoints of easy handleability, availability and low-cost that $R^2$, $R^3$ and $R^5$ in the formulae (1) and (2) are each independently cyclohexyl group or a cyclohexyl derivative group having 7 to 12 carbon atoms with the proviso that $R^6$, $R^8$ and $R^9$ in the formulae (2) and (3) are each independently an alkyl or alkenyl group having 8 to 20 carbon atoms. In particular, it is the most desirable that $R^2$, $R^3$ and $R^5$ in the formulae (1) and (2) are each independently cyclohexyl group or a cyclohexyl derivative group having 7 to 8 carbon atoms, with the proviso that $R^6$, $R^8$ and $R^9$ in the formulae (2) and (3) are each independently alkyl or alkenyl group having 12 to 19 carbon atoms.

The lower limit of the content of the diurea compound (a) in the urea-urethane thickening agent (A) is 20 mole %, preferably 40 mole %, still preferably 50 mole % based on the total amount of the components (a) to (c), while the upper limit thereof is 95 mole %, preferably 85 mole % based thereon. The diurea compounds to be used as the component (a) include not only a single structure compound but also a plurality of diurea compounds different from each other in structure, as far as they meet the above definitions given to $R^1$ to $R^3$ in the formula (1).

The lower limit of the content of the urea-urethane compound (b) in the thickening agent (A) is 4 mole %, preferably 5 mole %, still preferably 15 mole % based on the total amount of the components (a) to (c), while the upper limit thereof is 50 mole %, preferably 40 mole % based thereon. The urea-urethane compounds to be used as the component (b) include not only a single structure compound but also a plurality of urea-urethane compounds different from each other in structure, as far as they meet the above definitions given to $R^4$ to $R^6$ in the formula (2).

The lower limit of the content of the diurethane compound (c) in the thickening agent (A) is 1 mole %, preferably 3 mole % based on the total amount of the components (a) to (c), while the upper limit thereof is 50 mole %, preferably 20 mole %, still preferably 10 mole % based thereon. The diurethane compounds to be used as the component (c) include not only a single structure compound but also a plurality of diurethane compounds different from each other in structure, as far as they meet the above definitions given to $R^7$ to $R^9$ in the formula (3).

When the content of at least one of the components (a) to (c) deviates from the above-specified range, the resulting thickening agent will be poor in the ability to thicken a grease and the grease composition containing the same will be poor in shear stability and in the ability to keep the induced thrust at a low level even after long-time revolution, unfavorably.

Although the urea-urethane thickening agent to be used as the component (A) in this invention comprises a mixture of the above component (a) to (c) at a specific ratio, it is also essential in this invention that the ratio of the number of amino groups (i.e., the total number of $R^2$—NH—, $R^3$—NH— and $R^5$—NH— groups) to the number of alkoxy groups (i.e., the total number of $R^6$—O—, $R^8$—O— and $R^9$—O— groups) lies between 40:60 and 95:5, preferably between 70:30 and 95:5, still preferably between 75:25 and 90:10. When the content of the amino groups is less than 40%, the resulting thickening agent will be poor in the ability to thicken a grease and the grease composition containing the same will be poor in shear stability, while when it exceeds 95%, the resulting grease composition will be poor in the objective ability to keep the induced thrust at a low level even after long-time revolution. Thus, it is unfavorable that the grease composition of this invention contains both too high an amount of amino groups and too low an amount thereof.

Although the process for preparing the urea-urethane thickening agent (A) is not particularly limited but may be any one, a process for preparing a thickening agent of this invention will now be described as a concrete example in case of the thickening agent comprising compounds represented by the general formulae (1) to (3) wherein $R^1$, $R^4$ and $R^7$ are identical with each other, $R^2$, $R^3$ and $R^5$ are identical with each other and wherein $R^6$, $R^8$ and $R^9$ are identical with each other.

The component (A) can be obtained by preparing a diurea compound (a) by reacting a diisocyanate represented by the general formula: OCN—$R^1$—NCO with a primary amine represented by the general formula: $R^2$—$NH_2$, separately by preparing a urea-urethane compound (b) by reacting a diisocyanate represented by the general formula: OCN—$R^1$—NCO with a primary amine represented by the general forumla: $R^2$—$NH_2$ and an alcohol represented by the general formula: $R^6$—OH, further separately by preparing a diurethane compound (c) by reacting a diisocyanate represented by the general formula: OCN—$R^1$—NCO with an alcohol represented by the general formula: $R^6$—OH, and thereafter by mixing these components (a), (b) and (c).

In general, however, the component (A) can be prepared in one step by reacting a diisocyanate represented by the general formula: OCN—$R^1$—NCO with a primary amine represented by the general formula: $R^2$—$NH_2$ simultaneously with an alcohol represented by the general formula: $R^6$—OH.

More precisely, the component (A) can be prepared by mixing a primary amine represented by the general formula: $R^2$—$NH_2$ with an alcohol represented by the general formula: $R^6$—OH at a mole ratio ranging from 40:60 to 95:5 to obtain a mixture, and then by reacting the obtained mixture with a diisocyanate represented by the general formula: OCN—$R^1$—NCO generally at a temperature of 10 to 200° C. under sufficient stirring. In this reaction, a suitable solvent can be used, and examples of such a solvent are volatile ones such as benzene, toluene, xylene, hexane, petroleum ether, petroleum naphtha, diisobutyl ether and carbon tetrachloride; and lube base oils useful as the first component in this invention. Alternatively, the diisocyanate may be reacted with the primary amine not simultaneously with the alcohol but separately from the alcohol.

The urea-urethane thickening agent thus prepared is mixed with a proper amount of a lube base oil to form a grease, with the proviso that when the thickening agent is prepared by the use of a volatile solvent, the solvent must be removed prior to the mixing. When the thickening agent is prepared by the use of a lube base oil as a solvent, the resulting reaction mixture of the diisocyanate, the primary amine, the alcohol and the lube base oil may be used as a grease composition, or alternatively an additional lube oil may be added to the resulting reaction mixture to form a grease composition if required.

Although the above-mentioned process is one for preparing a component (A) comprising compounds represented by the general formulae (1) to (3) wherein $R^1$, $R^4$ and $R^7$ are identical with each other, $R^2$, $R^3$ and $R^5$ are identical with each other and wherein $R^6$, $R^8$ and $R^9$ are identical with each other, a mixture comprising a plurality of diurea compounds, a plurality of urea-urethane compounds and a plurality of diurethane compounds can also be prepared by using a mixture of diisocyanates of the general formula: OCN—$R^1$—NCO which are different in $R^1$, a mixture of primary amines of the general formula: $R^2$—$NH_2$ which are different in $R^2$, and/or a mixture of alcohols of the general formula: $R^6$—OH which are different in $R^6$.

More specific examples of the urea-urethane thickening agent (A) are those described in Japanese Patent Appln. Laid-Open Gazette No. 9296/89.

Although the grease composition for constant-velocity joints according to this invention may contain the urea-urethane thickening agent (A) in an arbitrary amount, it is desirable that the lower limit of the content of the thickening agent (A) is 2% by mass, more desirably 5% by mass based on the total amount of the grease composition, while the upper limit thereof is 25% by mass, more desirably 15% by mass. When the content of the component (A) is less than 2% by mass, the resulting composition will fail in taking the form of a satisfactory grease owing to its poor thickening effect, while when it exceeds 25% by mass, the resulting composition will be too hard to exhibit satisfactory lubricating performance.

The component (B) contained in the grease composition according to this invention comprises at least one compound selected from the group consisting of oxidized paraffins, diphenyl hydrogenphosphite and hexamethylphosphoric triamide.

Examples of the oxidized paraffins are those prepared by oxidizing petroleum waxes (such as paraffin wax, microcrystalline wax and petrolatum) and synthetic waxes (such as polyethylene wax). Although oxidized waxes having various properties can be used in this invention, it is desirable from the standpoints of the oxidation stability and rust preventing characteristics of the composition to use an oxidized wax having a saponification value of 30 to 200 mgKOH/g, more preferably 50 to 150 mgKOH/g as stipulated in JIS K 2503, and a total acid number of 2 to 20 mgKOH/g, more preferably 5 to 15 mgKOH/g as stipulated in JIS K 2501.

The term "diphenyl hydrogenphosphites" in this specification generally refers to the compounds represented by the following formulae (4) and (5):

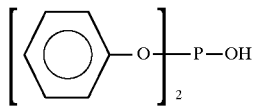

(4)

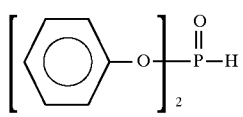

(5)

Further, the term "hexamethylphosphoric triamide" used in this specification refers to the compound represented by the following formula (6):

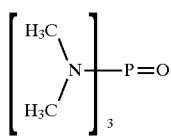

(6)

The component (B) contained in the grease composition according to this invention may be one member selected from the group consisting of oxidized paraffins, diphenyl hydrogenphosphites and hexamethylphosphoric triamide, or a mixture of two or more members selected from above group at an arbitrary ratio. Preferable examples of such a mixture are mixtures of oxidized waxes different from each other in properties; those of oxidized waxes and diphenyl hydrogenphosphites; those of oxidized waxes and hexamethylphosphoric triamide; those of diphenyl hydrogenphosphites and hexamethylphosphoric triamide; and those of oxidized paraffins, diphenyl hydrogenphosphites and hexamethylphosphoric triamide.

Although the grease composition for constant-velocity joints according to this invention may contain the component (B) in an arbitrary amount, it is generally desirable that the lower limit of the total content of the component (B) is 0.5% by mass, more desirably 1% by mass based on the total amount of the grease composition, while the upper limit thereof is 10% by mass, more desirably 5% by mass. When the total content of the component (B) is less than 0.5% by mass, the resulting composition will be poor in the ability to keep the induced thrust at a low level unfavorably, while when it exceeds 10% by mass, the resulting composition will be too poor in the ability to keep the induced thrust at a low level to reflect such a high content of the component (B), so that the use of the component (B) in such a high content will be uneconomic.

The component (C) contained in the grease composition according to this invention comprises at least one organo-molybdenum compound selected from the group consisting of molybdenum dithiophosphates and molybdenum dithio-carbamate.

Examples of the molybdenum dithiophosphates according to this invention are compounds represented by the following general formula (7):

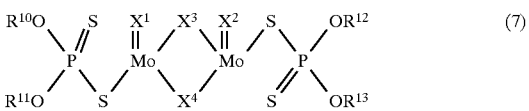

(7)

wherein $R^{10}$, $R^{11}$, $R^{12}$ and $R^{13}$ are each independently hydrocarbon group such as an alkyl group having 2 to 30 carbon atoms, preferably having 5 to 18 carbon atoms, still preferably having 5 to 12 carbon atoms or an (alkyl)aryl group having 6 to 18 carbon atoms, preferably having 10 to 15 carbon atoms; and wherein $X^1$, $X^2$, $X^3$ and $X^4$ are each independently sulfur or oxygen.

The alkyl group may be any of linear and branched primary alkyl groups, linear and branched secondary alkyl groups, and linear and branched tertiary alkyl groups. Preferable specific examples thereof are ethyl group, n-propyl group, isopropyl group, linear and branched butyl groups, linear and branched pentyl groups, linear and branched hexyl groups, linear and branched octyl groups, linear and branched decyl groups, linear and branched dodecyl groups, linear and branched tridecyl groups, linear and branched tetradecyl groups, linear and branched pentadecyl groups, linear and branched hexadecyl groups, linear and branched heptadecyl groups, and linear and branched octadecyl groups. On the other hand, preferable specific examples of the (alkyl)aryl are phenyl group, tolyl group (including all of the substitutional isomers thereof), ethylphenyl groups (including all of the substitutional isomers thereof), linear and branched propylphenyl groups (including all of the substitutional isomers thereof), linear and branched butylphenyl groups (including all of the substitutional isomers thereof), linear and branched pentylphenyl groups (including all of the substitutional isomers thereof), linear and branched hexylphenyl groups (including all of the substitutional isomers thereof), linear and branched octylphenyl groups (including all of the substitutional isomers thereof), linear and branched nonylphenyl groups (including all of the substitutional isomers thereof), linear and branched decylphenyl groups (including all of the substitutional isomers thereof), liner and branched undecylphenyl groups (including all of the substitutional isomers thereof), and linear and branched dodecylphenyl groups (including all of the substitutional isomers thereof).

Specific examples of the molybdenum dithiophosphate to be still preferably used as the component (C) are molybdenum sulfide diethyl dithiophosphate, molybdenum sulfide dipropyl dithiophosphate, molybdenum sulfide dibutyl dithiophosphate, molybdenum sulfide dipentyl dithiophosphate, molybdenum sulfide dihexyl dithiophosphate, molybdenum sulfide dioctyl dithiophosphate, molybdenum sulfide didecyl dithiophosphate, molybdenum sulfide didodecyl dithiophosphate, molybdenum sulfide di(butylphenyl) dithiophosphate, molybdenum sulfide di(nonylphenyl) dithiophosphate, molybdenum oxysulfide diethyl dithiophosphate, molybdenum oxysulfide dipropyl dithiophosphate, molybdenum oxysulfide dibutyl dithiophosphate, molybdenum oxysulfide dipentyl dithiophosphate, molybdenum oxysulfide dihexyl dithiophosphate, molybdenum oxysulfide dioctyl dithiophosphate, molybdenum oxysulfide didecyl dithiophosphate, molybdenum oxysulfide didodecyl dithiophosphate, molybdenum oxysulfide di(butylphenyl) dithiophosphate, molybdenum oxysulfide di(nonylphenyl) dithiophosphate, and mixtures of them.

Examples of the molybdenum dithiocarbamates according to this invention are the compounds represented by the following general formula (8):

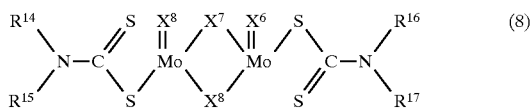

wherein $R^{14}$, $R^{15}$, $R^{16}$ and $R^{17}$ are each independently hydrocarbon group such as an alkyl group having 1 to 24 carbon atoms, preferably having 4 to 13 carbon atoms or an (alkyl)aryl group having 6 to 24 carbon atoms, preferably having 10 to 15 carbon atoms; and $X^5$, $X^6$, $X^7$ and $X^8$ are each independently sulfur or oxygen.

The alkyl group may be any of linear and branched primary alkyl group, linear and branched secondary alkyl group and linear and branched tertiary alkyl group. Preferable specific examples thereof are ethyl group, n-propyl group, isopropyl group, linear and branched butyl groups, linear and branched pentyl groups, linear and branched hexyl groups, linear and branched octyl groups, linear and branched decyl groups, linear and branched dodecyl groups, linear and branched tridecyl groups, linear and branched tetradecyl groups, linear and branched pentadecyl groups, linear and branched hexadecyl groups, linear and branched heptadecyl groups, and linear and branched octadecyl groups. On the other hand, preferable specific examples of the (alkyl)aryl are phenyl group, tolyl group (including all of the substitutional isomers thereof), ethylphenyl (including all of the substitutional isomers thereof), linear and branched propylphenyl groups (including all of the substitutional isomers thereof), linear and branched butylphenyl groups (including all of the substitutional isomers thereof), linear and branched pentylphenyl groups (including all of the substitutional isomers thereof), linear and branched hexylphenyl groups (including all of the substitutional isomers thereof), linear and branched octylphenyl groups (including all of the substitutional isomers thereof), linear and branched nonylphenyl groups (including all of the substitutional isomers thereof), linear and branched decylphenyl groups (including all of the substitutional isomers thereof), liner and branched undecylphenyl groups (including all of the substitutional isomers thereof), and linear and branched dodecylphenyl groups (including all of the substitutional isomers thereof).

Specific examples of the molybdenum dithiocarbamate to be still preferably used as the component (C) are molybdenum sulfide diethyldithiocarbamate, molybdenum sulfide dipropyldithiocarbamate, molybdenum sulfide dibutyldithiocarbamate, molybdenum sulfide dipentyldithiocarbamate, molybdenum sulfide dihexyldithiocarbamate, molybdenum sulfide dioctyldithiocarbamate, molybdenum sulfide didecyldithiocarbamate, molybdenum sulfide didodecyldithiocarbamate, molybdenum sulfide di(butylphenyl)dithiocarbamate, molybdenum sulfide di(nonylphenyl)dithiocarbamate, molybdenum oxysulfide diethyldithiocarbamate, molybdenum oxysulfide dipropyldithiocarbamate, molybdenum oxysulfide dibutyldithiocarbamate, molybdenum oxysulfide dipentyldithiocarbamate, molybdenum oxysulfide. dihexyldithiocarbamate, molybdenum oxysulfide dioctyldithiocarbamate, molybdenum oxysulfide didecyldithiocarbamate, molybdenum oxysulfide didodecyldithiocarbamate, molybdenum oxysulfide di(butylphenyl)dithiocarbamate, molybdenum oxysulfide di(nonylphenyl)dithiocarbamate, and mixtures of them.

In this invention, a mixture of one or more of the above molybdenum dithiophosphates and one or more of the above molybdenum dithiocarbamates at an arbitrary ratio can preferably be used as the component (C).

Although the grease composition for constant-velocity joints according to this invention may contain the component (C) in an arbitrary amount, it is generally desirable that the lower limit of the total content of the component (C) is 0.1% by mass, preferably 0.5% by mass, more preferably 1.0% by mass based on the total amount of the grease composition, while the upper limit thereof is 15.0% by mass, preferably 10.0% by mass, most preferably 7.0% by mass. When the total content of the component (C) is less than 0.1% by mass, the resulting composition will not suppress the induced thrust to a sufficiently low level unfavorably, while when it exceeds 15.0% by mass, the induced thrust will not be lowered to such a level as to reflect such a high content of the component (C), so that the use of the component (C) in such a high content will be uneconomic unfavorably.

According to this invention, a grease composition for constant-velocity joints having excellent performance characteristics can be prepared merely by adding the above components (A) to (C) to a lube base oil. In order to further improve the composition in its performance without impairing the excellent performance characteristics, however, various additives may be added to the composition. Examples of such additives are solid lubricants, extreme-pressure agents, antioxidants, oiliness improvers, rust inhibitors, viscosity index improvers, and so on. These additives may be used singly or in the form of a mixture of two or more of them.

Specific examples of the solid lubricants are graphite, boron nitride, graphite fluoride, polytetrafluoroethylene, molybdenum disulfide, antimony sulfide, and borates of alkali metals and alkaline earth metals.

Specific examples of the extreme-pressure agents are sulfur-containing ones such as monosulfides, disulfides, sulfoxides and sulfinates; phosphorus-containing ones such as phosphates, phosphites, phosphinates, phophonates, and amine salts thereof; chlorine-containing ones such as chlorinated paraffins and chlorinated esters; and zinc dithiophosphate.

Specific examples of the antioxidants are phenolic ones such as 2,6-di-t-butylphenol and 2,6-di-t-butyl-p-cresol; amines such as dialkyldiphenylamines, phenyl-α-naphthylamine and p-alkylphenyl-α-naphthylamines; sulfur-containing ones; and phenothiazine-type ones.

Specific examples of the oiliness improvers are amines such as laurylamine, myristylamine, palmitylamine, stearylamine and oleylamine; higher alcohols such as lauryl alcohol, myristyl alcohol, palmityl alcohol, stearyl alcohol and oleyl alcohol; higher fatty acids such as lauric acid, myristic acid, palmitic acid, stearic acid and oleic acid; fatty acid esters such as methyl laurate, methyl myristate, methyl palmitate, methyl stearate and methyl oleate; amides such as laurylamide, myristylamide, palmitylamide, stearylamide and oleylamide; and fats and oils.

Specific examples of the rust inhibitors are metal soaps; synthetic sulfonates such as petroleum sulfonate, alkylbenzenesulfonates and dinonyl-naphthalenesulfonates; partial esters of higher alcohols such as fatty acid esters of sorbitan; amines; phosphoric acid; and phosphates.

Specific examples of the viscosity index improvers are polymethyl methacrylate, polyisobutylene and polystyrene.

Although these additives may be added in arbitrary amounts, it is generally desirable that the total content of them is 20% by mass or below, more desirably 10% by mass or below based on the total amount of the grease composition.

The grease composition of this invention can suitably be used for plunging type constant-velocity joints, particularly tripod type constant-velocity joints.

The details of this invention will now be illustrated more specifically by referring to the following Examples and Comparative Examples, though this invention is not limited by them at all.

Examples 1 to 4 and Comparative Examples 1 to 8

Urea-urethane base greases A and B (as the base grease) which will be described below and various additives were kneaded in the ratios specified in Table 1 to prepare homogeneous grease compositions for constant-velocity joints according to this invention (Examples 1 to 4).

Separately, grease compositions for comparison were each prepared by using lithium soap base grease C (Comparative Examples 1 and 2), diurea base grease D (Comparative Examples 3 and 4) or diurea base grease E (Comparative Examples 5 and 6) as the base grease, without the component (C) (Comparative Example 7) or the component (B) (Comparative Example 8).

The base greases used will now be described.

Urea-urethane base grease A

A urea-urethane base grease A was prepared experimentally as follows:

Diphenylmethane-4,4'-diisocyanate was reacted with cyclohexylamine and octadecyl alcohol in a mole ratio of 5:8:2 in a proper amount of a refined mineral oil having a kinematic viscosity of 10.5 $mm^2/s$ at 100° C. to obtain a reaction mixture, and then the obtained reaction mixture was dispersed in such an amount of the refined mineral oil as to give a reaction mixture content of 10% by mass based on the total amount of the urea-urethane base grease A.

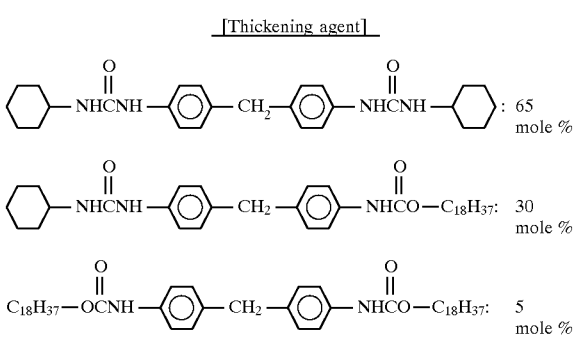

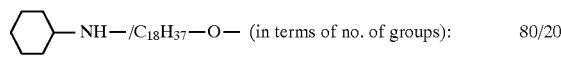

Urea-urethane base grease B

A urea-urethane base grease B was prepared experimentally as follows:

2,4-2,6-tolylene diisocyanate was reacted with cyclohexylamine and dodecyl alcohol in a mole ratio of 5:7:3 in a proper amount of the same refined mineral oil as one used in the preparation of urea-urethane base grease A to obtain a reaction moxture, and then the obtained reaction mixture was dispersed in such an amount of the refined mineral oil as to give a reaction mixture content of 18% by mass based on the total amount the urea-urethane base grease B.

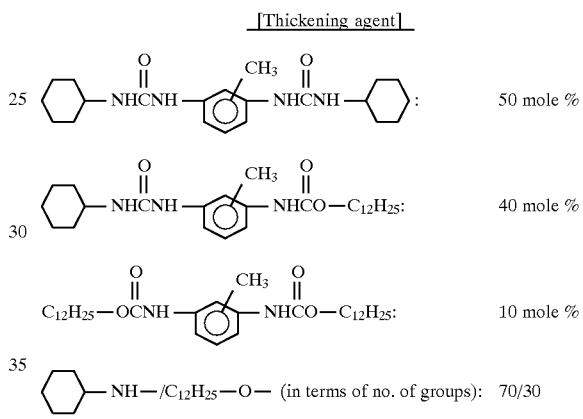

Lithium soap base grease C

A lithium soap base grease C was prepared experimentally as follows:

12-hydroxystearic acid was reacted with lithium hydroxide in a mole ratio of 1:1 under heating in a proper amount of the same refined mineral oil as one used in the preparation of urea-urethane base grease A to obtain lithium 12-hydroxystearate, and then the obtained lithium 12-hydroxystearate was dispersed in such an amount of the refined mineral oil as to give a lithium 12-hydroxystearate content of 8% by mass based on the total amount of the lithium soap base grease C.

Diurea base grease D

A diurea base grease D was prepared experimentally as follows:

Diphenylmethane-4,4'-diisocyanate was reacted with cyclohexylamine in a mole ratio of 1:2 in a proper amount of the same refined mineral oil as one used in the preparation of urea-urethane base grease A to obtain a reaction mixture, and then the obtained reaction mixture was dispersed in such an amount of the refined mineral oil as to give a reaction mixture content of 15% by mass based on the total amount of the diurea base grease D.

[Thickening agent]

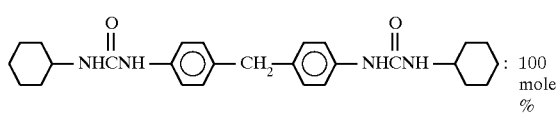 : 100 mole %

Diurea base grease E

A diurea base grease E was prepared experimentally as follows:

Diphenylmethane-4,4'-diisocyanate was reacted with octylamine and dodecylamine in a mole ratio of 5:8:2 in a proper amount of the same refined mineral oil as one used in the preparation of urea-urethane base grease A to obtain a reaction mixture, and then the obtained reaction mixture was dispersed in such an amount of the refined mineral oil as to give a reaction mixture content of 8% by mass based on the total amount of the diurea base grease E.

[Thickening agent]

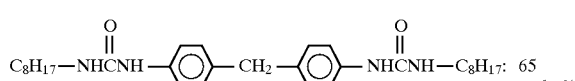 65 mole %

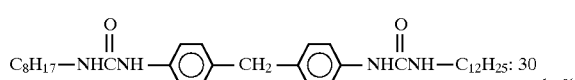 30 mole %

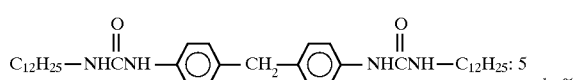 5 mole %

$C_8H_{17}$—NH—/$C_{12}H_{25}$—NH— (in terms of no. of groups): 80/20

These grease compositions were subjected to Performance test 1 which will be described, and the results are given in Table 1. Further, the grease compositions of Example 1 and Comparative Example 5 were also subjected to Performance test 2 which will be described, and the results are given in FIG. 1.

[Performance test 1]

Each sample grease was charged into a plunging tripod type joint, and then the resulting joint was operated at a speed of 150 rpm and an operating angle of 7° under loading of a constant torque (outer ring driving) for a predetermined time to determine the induced thrust generated during the operation. Thus, the joint was evaluated for average induced thrust and the rate of variation in induced thrust.

$$\text{*rate of variation in induced thrust (\%)} = \frac{\text{max. induced thrust} - \text{min. induced thrust}}{\text{av. induced thrust}} \times 100$$

[Performance test 2]

The grease compositions of Example 1 and Comparative Example 5 were each charged into a plunging tripod type joint, and then the resulting joints were operated at a speed of 150 rpm and an operating angle of 7° under loading of varying torque (outer ring driving). Thus, the joints were evaluated for variation in induced thrust.

TABLE 1

| | | | 1 | 2 | 3 | 4 | 1 | 2 | 3 | 4 | 5 | 6 | 7 | 8 |
|---|---|---|---|---|---|---|---|---|---|---|---|---|---|---|
| Compns. (% by mass) | base grease | urea-urethane base grease A | 95.5 | — | 95.5 | — | — | — | — | — | — | — | 97.0 | — |
| | | urea-urethane base grease B | — | 95.0 | — | 97.0 | — | — | — | — | — | — | — | 96.0 |
| | | lithium soap base grease C | — | — | — | — | 95.5 | 95.0 | — | — | — | — | — | — |
| | | diurea base grease D | — | — | — | — | — | — | 95.5 | 95.5 | — | — | — | — |
| | | diurea base grease E | — | — | — | — | — | — | — | — | 95.5 | 95.5 | — | — |
| | additives | oxidized paraffin 1) | 1.0 | 0.5 | 1.0 | — | 1.0 | 0.5 | 1.0 | 1.0 | 1.0 | 1.0 | 2.0 | — |
| | | diphenyl hydrogenphosphite | 0.5 | — | — | 0.5 | 0.5 | — | 0.5 | — | 0.5 | — | 1.0 | — |
| | | hexamethylphosphoric triamide | — | 0.5 | 0.5 | 1.0 | — | 0.5 | — | 0.5 | — | 0.5 | — | — |
| | | molybdenum dithiophosphate 2) | 3.0 | 2.0 | — | 1.5 | 3.0 | 2.0 | 3.0 | — | 3.0 | — | — | 2.0 |
| | | molybdenum dithiocarbamate 3) | — | 2.0 | 3.0 | — | — | 2.0 | — | 3.0 | — | 3.0 | — | 2.0 |
| consistency 60W 4) | | | 326 | 311 | 324 | 308 | 325 | 309 | 319 | 307 | 310 | 301 | 320 | 309 |
| Performance test I | av. induced thrust (N) | | 75 | 81 | 78 | 94 | 92 | 84 | 80 | 76 | 78 | 81 | 171 | 82 |
| | rate of variation in induced thrust (%) | | 8.6 | 9.5 | 10.3 | 17.6 | 36.8 | 43.1 | 41.4 | 56.0 | 29.6 | 38.0 | 113.4 | 78.6 |

The notes in the table will be supplemented below:
1) saponification value: 148 mgKOH/g, total acid number: 15 mgKOH/g 2) 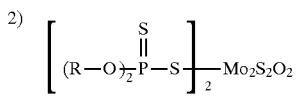 R: hexyl 3) 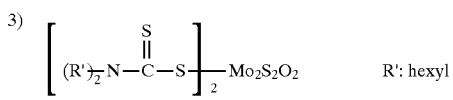 R': hexyl 4) according to JIS K 2220

As apparent from the results given in Table 1 and FIG. 1, the grease compositions of Examples for constant-velocity joints have such excellent performance characteristics that they can lower the induced thrust, that they can keep the lowered induced thrust even after long-time revolution, and that they can suppress the induced thrust to a low level not only when the joints are used under the low-torque but also when they are used under the high-torque.

On the other hand, the lithium soap base grease compositions of Comparative Examples 1 and 2, the diurea base grease compositions of Comparative Examples 3 to 6, and the grease composition of Comparative Example 8 not containing the component (B) are much inferior to the grease compositions of Examples in the ability to keep the induced thrust at a low level even after long-time revolution, though they can suppress the induced thrust to a low level in the initial stage. Further, the diurea base grease compositions represented by that of Comparative Example 5 are much inferior to the grease compositions of Examples in the induced thrust generated in the high-torque region.

Furthermore, the grease composition of Comparative Example 7 not containing the component (C) is much inferior to those of Examples in both the level of induced thrust and the ability to keep the induced thrust at a low level.

What is claimed is:

1. A grease composition for constant-velocity joints which is prepared by blending a lube base oil with (A) a urea-urethane thickening agent comprising a mixture of (a) 20 to 95 mole % of a diurea compound represented by the following formula (1):

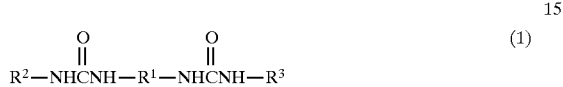

(b) 4 to 50 mole % of a urea-urethane compound represented by the following formula (2):

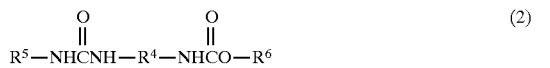

and (c) 1 to 50 mole % of a diurethane compound represented by the following formula (3):

with each mole percentage being based on the total amount of the components (a) to (c), wherein in the formulae (1) to (3), $R^1$, $R^4$ and $R^7$ are each independently a divalent aromatic hydrocarbon group having 6 to 15 carbon atoms; and $R^2$, $R^3$, $R^5$, $R^6$, $R^8$ and $R^9$ are each independently cyclohexyl group, a cyclohexyl derivative group having 7 to 12 carbon atoms, or an alkyl or alkenyl group having 8 to 20 carbon atoms, and wherein in said mixture a ratio of the number of amino groups (i.e., the total number of $R^2$—NH—, $R^3$—NH— and $R^5$—NH— groups) to the number of alkoxy groups (i.e., the total number of $R^6$—O—, $R^8$—O— and $R^9$—O— groups) lies between 40:60 and 95:5, (B) at least one compound selected from the group consisting of oxidized paraffins, diphenyl hydrogen-phosphite and hexamethylphosphoric triamide, and (C) at least one organomolybdenum compound selected from the group consisting of molybdenum dithiophosphate and molybdenum dithiocarbamate.

2. A grease composition according to claim 1, wherein a content of the urea-urethane thickening agent (A) ranges from 2 to 25% by mass, that of component (B) ranges from 0.5 to 10% by mass and wherein that of component (C) ranges from 0.1 to 15% by mass, each based on the total amount of the grease composition.

3. A grease composition according to claim 1, wherein a content of the urea-urethane thickening agent (A) ranges from 5 to 15% by mass, that of component (B) ranges from 1 to 5% by mass and wherein that of component (C) ranges from 0.5 to 10% by mass, each based on the total amount of the grease composition.

4. A grease composition according to claim 1, wherein in the formulae (1) and (2), $R^2$, $R^3$ and $R^5$ are each independently cyclohexyl group or cyclohexyl derivative group having 7 to 12 carbon atoms, and wherein in the formulae (2) and (3), $R^6$, $R^8$ and $R^9$ are each independently an alkyl or alkenyl group having 8 to 20 carbon atoms.

5. A grease composition according to claim 1, wherein in the formulae (1) and (2), $R^2$, $R^3$ and $R^5$ are each independently cyclohexyl group or cyclohexyl derivative group having 7 to 8 carbon atoms, and wherein in the formulae (2) and (3), $R^6$, $R^8$ and $R^9$ are each independently an alkyl or alkenyl group having 12 to 19 carbon atoms.

6. A grease composition according to claim 1, wherein in the formulae (1) to (3), $R^1$, $R^4$ and $R^7$ are each independently selected from divalent aromatic hydrocarbon groups represented by the following formulae:

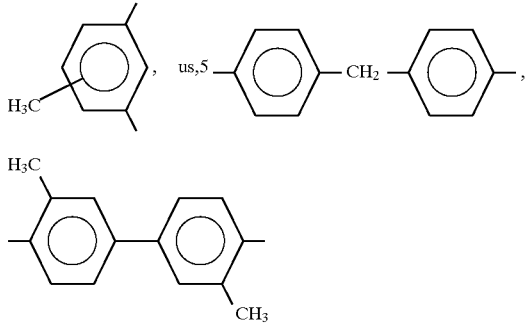

7. A grease composition according to claim 1, wherein a content of the diurea compound (a) in the urea-urethane thickening agent (A) ranges from 40 to 85 mole %, that of the urea-urethane compound (b) therein ranges from 5 to 40 mole % and wherein that of the diurethane compound (c) therein ranges from 3 to 20 mole %, each based on the total amount of components (a) to (c).

8. A grease composition according to claim 1, wherein a ratio of the total number of $R^2$—NH—, $R^3$—NH— and $R^5$—NH— groups to the total number of $R^6$—O—, $R^8$—O— and $R^9$—O—groups is between 70:30 and 95:5.

9. A grease composition according to claim 1, wherein said molybdenum dithiophosphate is compound represented by the following formula (7):

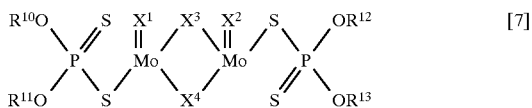

wherein $R^{10}$, $R^{11}$, $R^{12}$ and $R^{13}$ are each independently an alkyl group having 2 to 30 carbon atoms or an (alkyl)aryl group having 6 to 18 carbon atoms, and wherein $X^1$, $X^2$, $X^3$ and $X^4$ are each independently sulfur or oxygen.

10. A grease composition according to claim 1, wherein said molybdenum dithiocarbamate is compound represented by the following general formula (8):

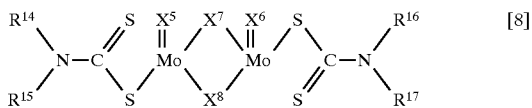

wherein $R^{14}$, $R^{15}$, $R^{16}$ and $R^{17}$ are each independently an alkyl group having 1 to 24 carbon atoms or an (alkyl)aryl group having 6 to 24 carbon atoms, and wherein $X^5$, $X^6$, $X^7$ and $X^8$ are each independently sulfur or oxygen.

* * * * *